United States Patent

Kim

[11] Patent Number: 6,159,235
[45] Date of Patent: Dec. 12, 2000

[54] SELFLOCK ANCHOR SCREW

[76] Inventor: Andrew C. Kim, 30213 Del Rey Rd., Temecula, Calif. 92591

[21] Appl. No.: 09/467,679

[22] Filed: Dec. 21, 1999

[51] Int. Cl.⁷ .................................................. A61B 17/04
[52] U.S. Cl. ............................................................ 606/232
[58] Field of Search ...................................... 606/232, 73

[56] References Cited

U.S. PATENT DOCUMENTS

| | | | |
|---|---|---|---|
| 5,718,706 | 2/1998 | Roger | 606/232 |
| 5,797,914 | 8/1998 | Leibinger | 606/73 |
| 5,827,291 | 10/1998 | Fucci et al. | 606/232 |
| 5,851,219 | 12/1998 | Goble et al. | 606/232 |
| 5,931,838 | 8/1999 | Vito | 606/73 |
| 5,964,783 | 10/1999 | Grafton et al. | 606/232 |
| 6,045,573 | 4/2000 | Wenstrom, Jr. | 606/232 |

*Primary Examiner*—Paul J. Hirsch
*Attorney, Agent, or Firm*—Baker & Maxham

[57] ABSTRACT

A self-locking tissue anchoring screw comprises an elongated shank having a proximal end and a distal end, a threaded portion of the shank tapering to a point at the distal end, a cylindrical journal formed on the shank between opposing shoulders adjacent the proximal end a clamping ring having an inner diameter greater than the cylindrical journal mounted on the journal for receiving and clamping a suture upon insertion of the screw, and a head at the proximal end adapted to receive a driver.

18 Claims, 1 Drawing Sheet

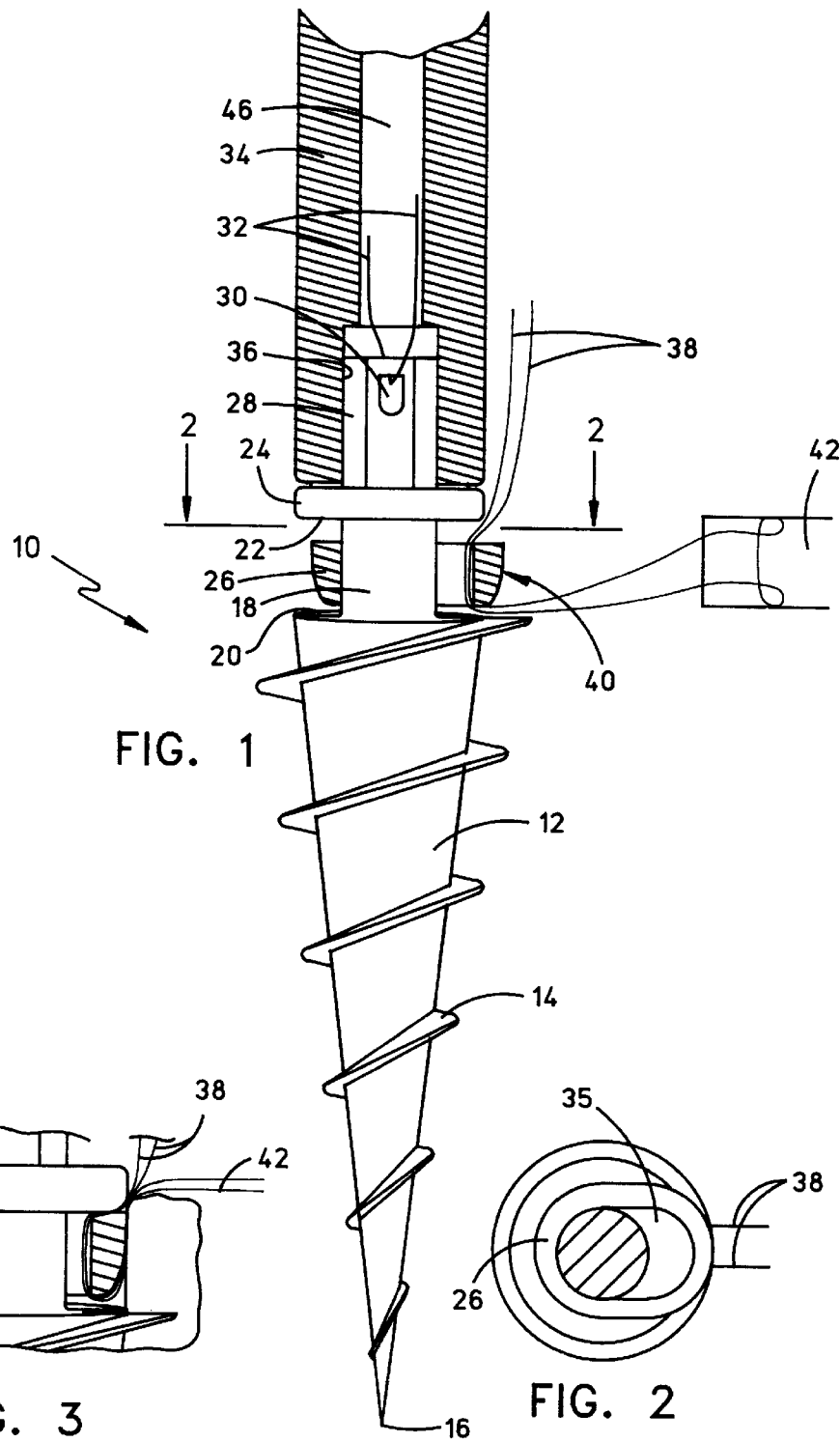

SELFLOCK ANCHOR SCREW

BACKGROUND OF THE INVENTION

The present invention relates to anchoring devices and pertains particularly to improved anchoring screws for tissue, including tendons, ligaments and the like.

Many anchoring devices for anchoring sutures, tendons and the like to bones are known. A common feature of these many devices is the way the anchor is applied. In most of these devices the anchor is first inserted into a bone with a suture connected in and coming out of the anchor. The suture is passed or secured into the soft tissue to be repaired. The soft tissue is then pulled or brought down to the anchor and the suture is tied to the anchor.

Frequently the soft tissue is under tension tending to pull it away from the anchor and the bone. In the process of tying a knot there is frequently a failure of achieving a tight contact or secure anchor of the soft tissue to the anchor. In addition, the tissue is often not brought into sufficient contact with the bone to enable reattachment.

There is a need for an improved anchoring device to overcome the above problems of the prior art by providing a more secure and tight soft tissue attachment to bones in a simple and effective manner.

SUMMARY AND OBJECTS OF THE INVENTION

The primary object of the present invention is to provide a simple and effective method and apparatus for the securing of soft tissue to a bone.

In accordance with a primary aspect of the present invention, an anchoring screw comprises an elongated shank having a proximal end and a distal end, a threaded portion at the distal end, a cylindrical journal portion extending axially from the threaded portion, a clamping ring mounted on the journal portion for receiving and clamping a suture upon insertion of the screw, a stop member for retaining the ring on the journal, and a head at the proximal end adapted to receive a driver.

BRIEF DESCRIPTION OF THE DRAWINGS

The above and other objects and advantages of the present invention will become apparent from the following description and the accompanying drawing wherein:

FIG. 1 is a side elevation view of an exemplary preferred embodiment of the invention;

FIG. 2 is a section view taken along lines 2—2 of FIG. 1; and

FIG. 3 is a detailed view showing the suture connection in position installed in a bone.

DETAILED DESCRIPTION OF THE PREFERRED EMBODIMENTS

Referring to FIGS. 1 and 2 of the drawing, there is illustrated an anchoring screw apparatus in accordance with an exemplary embodiment of the invention designated generally by the numeral 10, shown in an intermediate stage of securing a tendon to a bone 44. The illustrated embodiment comprises an elongated screw-like anchoring device having an elongated tapered shank 12 with threads 14 and tapering to a sharp point 16 at a forward end. The screw is essentially self-threading or taping and ordinarily does not need a pre-drilled bore. The shank is configured and formed with screw threads 14 for engaging and threading into a bone. The head end above the threaded portion axially thereof is formed with an elongated cylindrical journal portion 18 between a pair of opposing shoulders 20 and 22. The journal is formed as a reduced portion of the screw shank thereby forming shoulders 20 and 22. The shoulder 22 is formed by an annular flange 24 which functions as a stop for a suture receiving ring or sleeve 26 mounted on the journal.

A hex shaped tool stud or fitting 28 is formed on and extends axially from the head end of the screw to be engaged by a driving tool. The tool fitting may take any form adapted to be engaged by a driving tool such as a screw driver to rotate the screw and drive it into a bone. A suture receiving cross-bore 30 is formed in the tool fitting 28 for receiving a suture or engaging thread 32 for holding the screw in driving engagement with a screw driver 34. The screw driver is formed with a hex socket 36 for receiving or drivingly engaging hex head stud 28. The driver 34 is formed with an axial bore 46 through which is threaded the engaging thread 32 for holding the screw in engagement with the driver.

Referring to FIG. 2, the suture receiving ring 26 is shown to have an elongated or oblong configuration with a ring opening or aperature 35 for receiving a suture 38 against shoulder 22. The ring is also formed with an outer surface 40 that tapers from a larger diameter toward the head end of the screw to a lesser diameter toward the point of the screw. This surface forms a cam or cam-like surface that is engaged by the bone during installation to cam it into engagement with shoulder 22 of stop 24 for clamping the suture 38 and holding it between the ring and shoulder.

As shown in FIG. 2, the ring opening 35 is shown to have a width slightly larger than the diameter of the journal and a length that can be one and a half to about two times the diameter of the journal. This construction may be made by machining the entire structure including ring 26 in place from the stock of the screw. The ring may be either formed in the oval configuration or machined round and then bent into the oval configuration. It may also be made with the ring made separate, mounted over stop 24 and made or formed into the oblong shape. Alternatively the shoulder can be made as a separate member and secured by mechanical locking or other suitable fastening means to the screw shank after the ring is mounted.

In FIG. 1, the suture 38 is shown attached to tissue 42 such as a tendon and threaded through the ring 36 in preparation for attachment to a bone. In operation, a soft tissue repair starts with the step of selecting a suture 38 and passing it or threading it through the ends of a tissue 42 such as a tendon or ligament. The two ends of the suture 38 are inserted through the opening in ring 26 as shown. The screw is engaged or fitted to a driver as shown in FIG. 1 with the engagement thread 32 extending through the cross-bore 30 and along the bore 46 of the tool 34 to hold the screw 10 in place.

The threaded portion 12 of the screw is then inserted or driven into the desired bone surface or structure 44, as illustrated in FIG. 3. Once the threaded screw portion is buried in the bone and before the bone touches or engages the ring, the suture ends are pulled to the desired maximum tension to bring the soft tissue into contact or engagement with the anchor and with the bone. The soft tissue is pulled as close as possible to the bone, the screw is then screwed further into the bone so that the suture is buried in the bone, along with the ring, the stop block and the wrench head of the screw. The ring 26 is camed toward the center of the journal and its upper surface engages the suture and clamps or forces it against the shoulder 22 locking or clamping it in place. This locks the suture automatically to the anchor and the bone without the necessity of making or tying a knot. After the self-lock screw device is in place, a security knot may be made in the suture to avoid the risk of loosing the tension.

The screw assembly may be constructed of any suitable medical grade material such as stainless steel, tungsten, titanium, ceramic, plastic and other such materials.

The apparatus in accordance with the invention is ideal for arthroscopic rotator cuff repair. Passing a free suture to the rotator cuff tendon is much easier than passing an anchor suture through the soft tissue. Making an arthroscopic knot can be especially difficult when tension is present on the rotator cuff tendon. With this self-locking anchor screw repair of the rotator cuff tendon will be much simpler, easier and effective.

While I have illustrated and described my invention by means of specific embodiments, it is to be understood that numerous changes and modifications may be made therein without departing from the spirit and the scope of the invention as shown in the appended claims.

I claim:

1. A tissue anchoring screw comprising:
   an elongated shank having a proximal end and a distal end;
   a threaded portion at said distal end;
   a cylindrical journal portion extending axially from the threaded portion;
   a clamping ring mounted on said journal portion for receiving and clamping a suture upon insertion of the screw;
   a stop member for retaining said ring on said journal; and
   a head at said proximal end adapted to receive a driver.

2. An anchoring screw according to claim 1, wherein said ring has a generally oblong configuration an inner diameter with a width that is slightly larger than the journal and length that is greater than the diameter of said journal to receive a suture.

3. An anchoring screw according to claim 2, wherein said ring has an outer diameter surface that tapers from a greater diameter from said proximal end to a lesser diameter toward said distal end.

4. An anchoring screw according to claim 1, wherein said ring has an outer diameter that tapers from a greater diameter adjacent said proximal end to a lesser diameter adjacent said distal end.

5. An anchoring screw according to claim 4, wherein said ring has an axial length that is less than an axial length of said journal.

6. An anchoring screw according to claim 5, wherein said stop member is a radial flange at one end of said journal.

7. An anchoring screw according to claim 1, wherein said stop member is a radial flange at one end of said journal.

8. An anchoring screw according to claim 1, wherein said stop member is formed integral with the body of the screw.

9. An anchoring screw according to claim 1, wherein said threaded portion tapers to a point at said distal end.

10. An anchoring screw according to claim 1, wherein said elongated shank includes a cross bore at said head end.

11. An anchoring screw according to claim 1, wherein said journal is formed between two radial shoulders at said proximal end.

12. An anchoring screw according to claim 1, wherein said head is configured to receive a hex driver.

13. An anchoring screw according to claim 1, wherein said ring has an outer diameter that is about equal to the diameter of the threaded shank portion at the root of the threads.

14. A self-locking tissue anchoring screw comprising;
    an elongated shank having a proximal end and a distal end;
    a threaded portion of said shank tapering to a point at said distal end;
    a cylindrical journal formed on said shank between opposing shoulders adjacent said proximal end;
    a clamping ring having an inner diameter greater than said cylindrical journal mounted on said journal for receiving and clamping a suture upon insertion of the screw; and
    a head at said proximal end adapted to receive a driver.

15. An anchoring screw according to claim 14, wherein said ring has an outer diameter that tapers from a greater diameter adjacent said proximal end to a lesser diameter adjacent said distal end.

16. An anchoring screw according to claim 15, wherein said ring has an axial length that is less than the distance between said opposing shoulders.

17. An anchoring screw according to claim 15, wherein said head is formed to receive a hex driver and includes a transverse suture receiving bore.

18. A method of tissue repair comprising the steps of:
    providing an anchoring screw having a threaded shank with a journal between opposing shoulders at a head portion;
    providing a clamping ring on said journal for receiving and clamping a suture;
    securing a suture to a tissue to be anchored and threading said tissue through said ring; and
    inserting the screw into a bone to a depth for effectively clamping the suture between the ring and the screw.

* * * * *